United States Patent [19]

Rey et al.

[11] Patent Number: 4,857,059
[45] Date of Patent: Aug. 15, 1989

[54] RECHARGEABLE IMPLANTABLE DEVICE FOR DOSED AND REPEATED SELF-INJECTION OF MEDICAMENT

[75] Inventors: Pierre Rey, Lagny; Jacqueline Leandri, Paris; Clément Abbou, Fontenay sous Bois; Alain Sezeur, Cachan, all of France

[73] Assignee: Centre National de la Recherche Scientifique, Paris, France

[21] Appl. No.: 141,309

[22] PCT Filed: Apr. 24, 1987

[86] PCT No.: PCT/FR87/00138
 § 371 Date: Dec. 10, 1987
 § 102(e) Date: Dec. 10, 1987

[87] PCT Pub. No.: WO87/06473
 PCT Pub. Date: Nov. 5, 1987

[30] Foreign Application Priority Data

Apr. 24, 1986 [FR] France .............................. 86 05927

[51] Int. Cl.⁴ ................................................. A61M 5/00
[52] U.S. Cl. ..................................... 604/185; 604/181
[58] Field of Search ........................ 604/181, 183–186

[56] References Cited

U.S. PATENT DOCUMENTS 4,258,711 3/1981 Tucker et al. .
4,337,770 7/1982 Young et al. .
4,544,371 10/1985 Dormandy, Jr. et al. .
4,588,394 5/1986 Schulte et al. .
4,634,427 1/1987 Hannula et al. ...................... 604/185
4,710,177 12/1987 Smith et al. .......................... 604/185

FOREIGN PATENT DOCUMENTS 0138648 4/1985 European Pat. Off. .
0143503 6/1985 European Pat. Off. .
2569987 3/1986 France .

Primary Examiner—Stephen C. Pellegrino
Assistant Examiner—Kathleen A. Daley
Attorney, Agent, or Firm—Browdy and Neimark

[57] ABSTRACT

The implantable device for the repeated injection of medicament (20) in unitary does in at a frequency which is a function of the therapeutical treatment needs comprises essentially: a flexible reservoir (6) for the storage of the medicament. A first flexible connection tube (7) connecting the reservoir to an injection site (5) a small flexible balloon for the predosing and controlling of the injection of the medicament, a second flexible connection tube (9) connecting the small balloon (10) and the reservoir (6), a valve fitted with valve means (16) of the type responsive only to the pressure exerted to small balloon means (11) for controlling the flow rate for filling the small balloon (10), and provided on said second connection tube (9), a non-return valve (21) provided immediately upstream of the control balloon (10). Application to therapeutic treatments.

14 Claims, 1 Drawing Sheet

U.S. Patent    Aug. 15, 1989    4,857,059
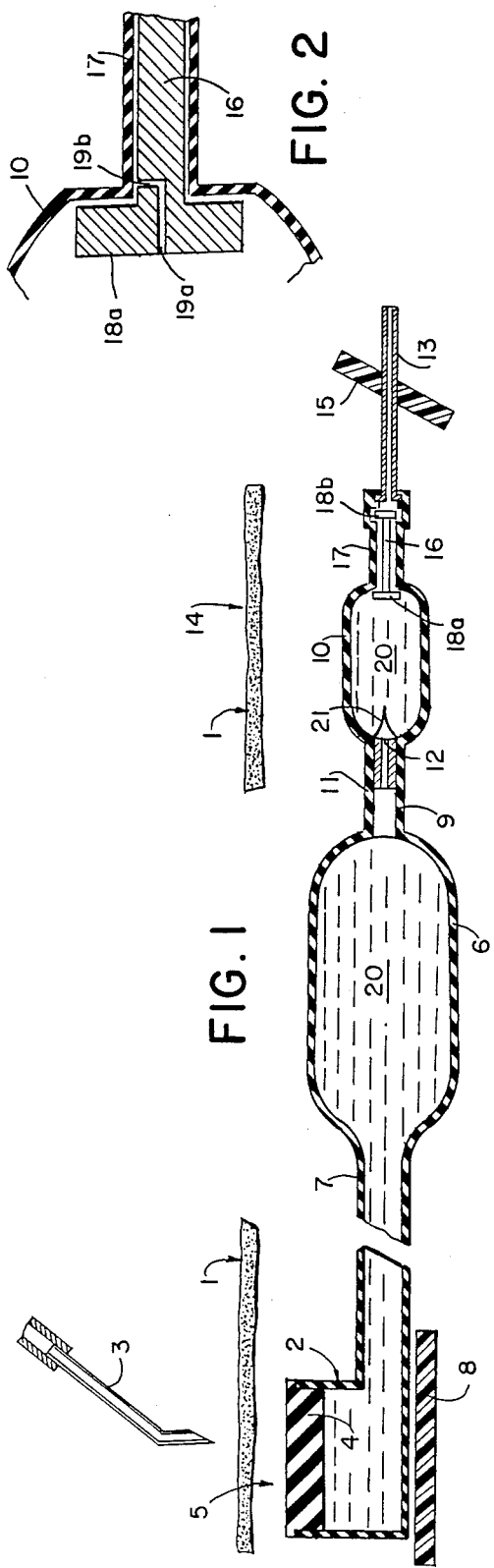
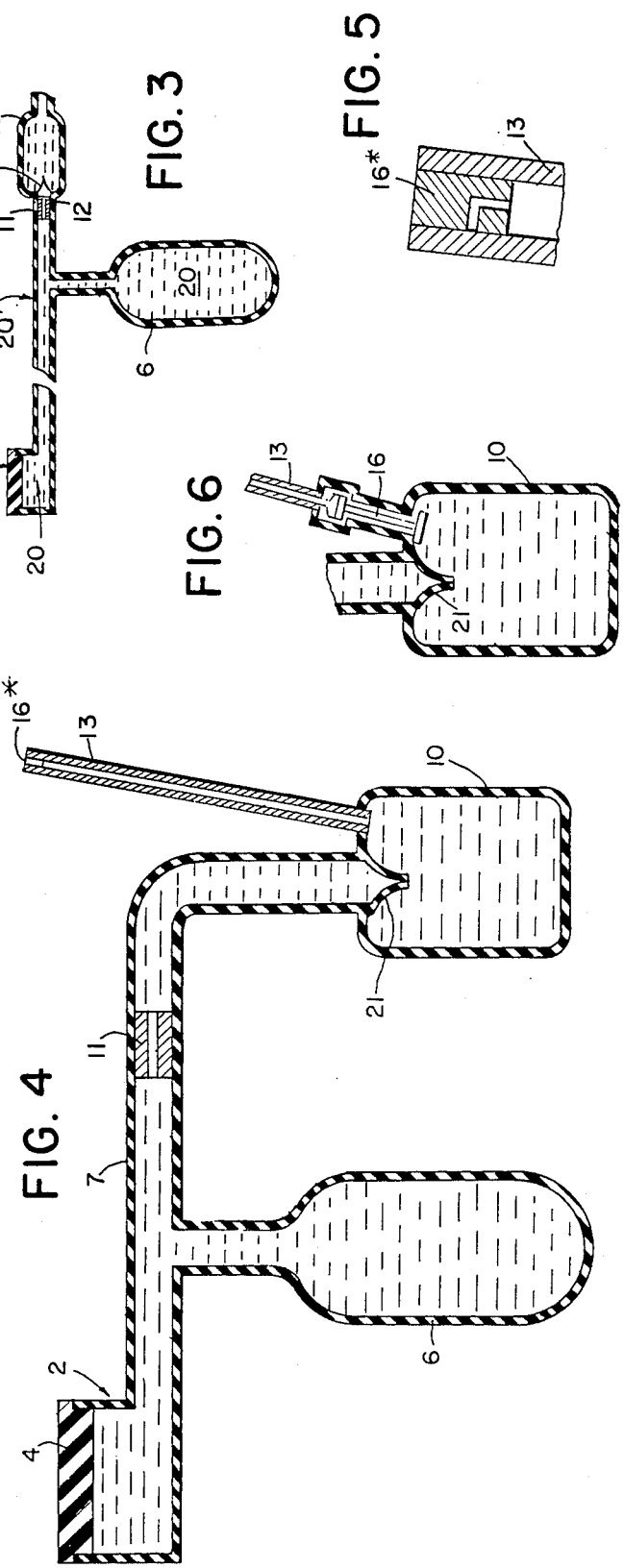

RECHARGEABLE IMPLANTABLE DEVICE FOR DOSED AND REPEATED SELF-INJECTION OF MEDICAMENT

The present invention relates to an implantable device for the repeated self-injection of a medicament, and more particularly analgesic, in unitary doses and at a frequency which is a function of the therapeutic treatment needs and in particular of the desired analgesic action.

At the present time, particularly in relation with drugs prescribed in pain-killing treatments, they are administered to a patient as a function of the state of gravity of his illness and the intensity of the painful syndrome.

either in isolated injections, which in numerous cases raises the problem of repeated pricks, or in a previously implated site in a subcutaneous position cooperating with a catheter implanted at the level of the analgesic action zone, this solution nevertheless not overcoming the problem of repeated pricks.

Several implantable devices of the above mentioned type exist, described more particularly in patents U.S. Pat. No. 4,588,394, FR-2 569 987 and EP-143 503 - which are however designed for avoiding involuntary interventions and which, therefore, do not prevent overdoses through undue (voluntary) intervention, particularly through forgetfulness - as well as in patents U.S. Pat. No. 4,193,397 and U.S. Pat. No. 4,258,711 which describe an "artificial pancreas" for the continuous administration of a medicament (called basal administration) possibly reinforced by an administration for confronting exceptional situations, particularly during meals (and corresponding to the administration of a "bolus" intended to flow progressively towards the concerned zone of the organism).

The purpose of the present invention is to provide a device for the repeated injection of unitary medicament doses and particularly analgesic, which answers better the requirements of practice than the devices known at the present time, particularly in that:

it makes possible the injection, without requiring a prick on the part of the patient himself, and depending on the requirements, in particular of the analgesic doses strictly required, pricks are required for supplying the medicament, particularly analgesic, and not for injecting this latter, so that their number is considerably reduced and two consecutive pricks are spaced very far apart in time, which substantially reduces the risks of infection and therefore makes it possible to provide for example intraspinal and no longer peridural injection, which in its turn reduces the effecient doses of analgesic by a factor at least equal to 3, and it ensures the necessary safety in use by preventing overdoses.

The present invention has as object a device for the repeated injection of medicament in unitary doses and at a frequency which is a function of the therapeutic treatment needs, said device being intended to be implanted in the body of a patient and comprising a site for injection of the medicament, intended to be implanted below the skin of the patient, an external means for supplying this site, comprising particularly a needle for pricking said site connected to a syringe or to a pump, and a catheter for injecting each unitary dose of medicament intended to be implanted in the therapeutic action zone, which device is characterized in that it further comprises:

a reservoir, made from a flexible plastic material such as silicone elastomer, intended for storing the medicament between two restocking operations by means of said syringe and through said injection site.

a first connection tube made from a flexible plastic material, such as that used for the reservoir, and connecting this reservoir to said injection site, a pre-dosed small balloon, having an inlet and an outlet and intended for controlling the injection of medicament, itself also made from a flexible plastic material, such as the one used for the reservoir, whose volume is calculated as a function of the unitary dose of medicament to be injected through said catheter and by pressure of this small balloon obtained by cutaneous digital deformation, a second tube for connection between the small balloon and the reservoir, it also like this latter being made from a flexible plastic material, a valve equipped with a valve means of the type responsive only to the pressure exerted on the small balloon, in that said second connection tube is provided with a means for controlling the flow rate of the medicament, which is disposed upstream of the small control balloon between this latter and the reservoir and which is intended to control the time for filling the small balloon and so the frequency of injection of the unitary dose of medicament contained in this latter, and in that a non-return valve is formed immediately upstream of the small control balloon.

In particular, the present invention has as object a device for the repeated injection of medicament in unitary doses and at a frequency which is a function of the therapeutic treatment needs, said device being intended to be implanted in the body of a patient and comprising:

a site for injection of the medicament, intended to be implanted below the skin of a patient, an external means for supplying this site, comprising more particularly a needle for pricking said site, connected to a syringe or to a pump, a catheter for injecting each unitary dose of medicament, intended to be implanted in the therapeutic action zone, a reservoir, made from a flexible plastic material such as a silicone elastomer, intended for storing the medicament between two restocking operations by means of said syringe and through said injection site, a first connection tube made from a flexible plastic material such as that used for the reservoir and connecting this reservoir to said injection site, a pre-dosed small balloon, a second tube for connection between the small balloon and the reservoir, it also being made like this latter from a flexible plastic material, a capillary for controlling the flowrate of the medicament disposed upstream of the small balloon, between this latter and the reservoir, so as to control the filling time of this small balloon, and also comprising:

a valve equipped with a valve means responsive only to the pressure, a small balloon, itself also made from a flexible plastic material such as that used for the reservoir, whose volume is calculated as a function of the unitary dose of medicament to be injected through said catheter and by pressure of this small balloon obtained by cutaneous digital deformation, said small balloon forming the means for controlling the injection of medicament in cooperation with the valve comprising said valve means, which valve means is sealingly gripped by the distal end of the catheter and is formed by a valve rod with means for initiating slackening of the distal end of the catheter under the effect of the pressure of medicament exerted by the cutaneous digital control of said small balloon.

In accordance with the invention, the device is further characterized in that the means for controlling the flowrate is formed by a tube which is provided with a micro-channel (or capillary) which has a diameter and a length defined as a function of the desired flowrate and whose external wall is sealingly fixed to the internal wall of the second connection tube.

It should be noted that the tubes (first and second) are made as a single piece with three branches, particularly in the form of a T or a Y, which makes it possible to choose the implantation zone of said reservoir in the organism of the patient, as a function of the needs, the means for controlling the filling rate being disposed in the branch of said piece which is connected to the small balloon.

In an advantageous device of the object of the invention, the inlet and the outlet of the small balloon are formed in the small control balloon at positions situated on the same side.

Besides the above arrangements, the invention further comprises other arrangements which will be clear from the following description.

The invention will be better understood with the help of the complement of description which follows, which refers to the accompanying drawings in, which:

FIG. 1 shows schematically the device of the invention implanted in an organism, FIG. 2 shows on a larger scale a detail of a valve means used in the device of FIG. 1.

FIG. 3 shows schematically a variant in the relative arrangement of the components of the device of the invention with respect to the arrangement illustrated in FIG. 1.

FIGS. 4 and 6 correspond to variants of construction of the device of the invention with respect to the representation of FIG. 3, FIG. 4 differing with respect to FIG. 6 in that the device comprises a valve means housed in the distal end of the catheter and whose design is different with respect to the valve means shown in FIGS. 1 and 6 (it is based on the Certificate of Addition Application FR-86 05928).

FIG. 5 illustrates on a larger scale a variant of the valve means used in FIG. 4.

It should however be understood that these drawings and the corresponding descriptive parts are given solely by way of illustration of the object of the invention, of which they in no wise form a limitation.

The device of the invention is shown schematically in FIG. 1 as being implanted in an organism (reference 1 designates the skin of a patient).

There will first of all be noted the presence of a cup 2 to be supplied with an analgesic liquid product 20 by means of a syringe (not shown) having a needle 3 of the so-called HUBERT type: to this end, the cup is provided with a plug 4 made from a material allowing hyperdermic injections, made more particularly from silicone elastomer.

This cup 2 and its plug 4 are intended to be implanted in a subcutaneous position and define an injection site 5 whose position is known by the doctor or the attendant nurse and, of course, by the patient.

The injection site 5 makes it possible to supply a flexible reservoir 6 through a flexible connecting tube 7.

A plate 8 made from "Dacron" fabric stabilizes the implantation of the injection site 5 with respect to the surrounding tissues of the patient, so that correspondance between this site 5 and the zone of skin 1 intended to be pricked is always respected: thus, there will always be the certainty of supplying the reservoir 6 when the skin 1 of the patient is pricked to acceed to site 5 with needle 3. The use of the stabilization fabric 8 answers then safety requirement measures.

Another connection tube 9 connects the reservoir 6 to a small flexible balloon 10 of predefined volume for injecting an analgesic dose, whose therapeutic dose is determined precisely by the volume of this small balloon. The time for filling this small balloon controls automatically the frequency of injection of the unitary analgesic dose contained in the small balloon, thus preventing overdoses.

The means for controlling the filling rate of the small balloon 10 is formed by a capillary tube 11. This capillary is provided with a micro-channel 12, whose flowrate is regulated by choosing an appropriate diameter and length and is housed in the connection tube 9; the filling rate is therefore definitely determined and in a precise way by construction.

Thus, the filling time of the small balloon 10 may be controlled, which may be variable and equal for example to 2, 4 or 6 hours and even longer up to 24 hours if required, depending on the desired injection frequency.

A catheter 13, which is implanted in the analgesic action zone, permits the injection of the analgesic dose contained in the small balloon 10 by manual or finger pressure on this small balloon effected through the skin at position 14 (known by the patient) where the small balloon is implanted.

A "Dacron" washer 15 surrounding the catheter 13 stabilizes the implantation of this latter with respect to the surrounding tissues, which is required so that the analgesic injection always takes place in the analgesic action zone and not in another zone.

Between the catheter 13 and the small balloon 10 is inserted a valve means allowing the analgesic to flow towards this catheter in response to a pressure exerted on the small balloon 10.

Advantageously this valve means is of the type described in the French patent application No. 83 14607 filed in the name of the applicant on Sept. 14th, 1983, namely that it is formed by a valve rod 16 which, in the rest condition, is sealingly gripped inside a sheath 17 connecting the small balloon 10 to the catheter 13 and is made from a flexible plastic material which shrinks when polymerized, which rod has at its end means for preventing its axial movement under the effect of the pressure exerted on the small balloon 10. These means for stabilizing rod 16 may be formed, in accordance with the arrangements described in the above French patent application No. 8314607 by disks 18a and 18b or by equivalent projections also described in this latter application.

In addition, the proximal and of the valve rod 16 may be provided (in accordance with the Certificate of Addition Application No. 86 05928 relating to said patent application No. 83 14607 and filed simultaneously with the present invention) with means for initiating slackening of sheath 17 sealingly gripping this rod 16, under the effect of the pressure of the analgesic contained in the small control balloon 10. As is recalled in FIG. 2, accompanying this description, the means for initiating slackening are advantageously formed by a blind axial channel 19a which is provided in the proximal end of the valve rod 16 and which communicates with the small balloon 10 and at least with one channel opening at the surface of the valve rod 16, at the level of the corresponding end of the internal surface of sheath 17, such as channel 19b.

It is evident that the essential difference existing in the use of said valve system (formed by the cooperation of a valve rod 16 and a sheath 17 sealingly gripping this rod), such as applied to the devices described in patent application No. 83 14607 and to certain arrangements of the Certificate of Addition Application relating thereto, with respect to the device of the present invention, consists in that in this latter case it is not a question of controlling the flow of a fluid external to the small control balloon 10, but rather the flow of a fluid contained inside this small balloon, namely the analgesic liquid product.

Furthermore, it goes without saying that it is possible to dispose the valve means at the level of the distal end of the catheter 13 instead of placing it between this latter and the small control balloon 10. In this case, it is advantageous to use a valve rod without end swellings, such as that shown in FIGS. 1b of the patient application No. 83 14607 and said addition application relating thereto, as well as in FIGS. 2 and 4 to 13 accompanying this Certificate of Addition Application.

In FIG. 3, a variant of the device of the invention is shown schematically in which the relative arrangement of its components is different with respect to that illustrated in FIG. 1. This varient comprises a tube 20 with three branches which is in the form of a T (but which could also be in the form of a Y) and providing the necessary connection between the injection site 5, reservoir 6 and the small balloon 10.

This variant is particularly advantageous because it makes is possible to choose the implantation zone for reservoir 6 in the organism of the patient, as a function of the needs.

It goes without saying, in this case, that the capillary tube 11 is disposed in the branch of the tube 20 connected to the small balloon 10.

In so far as the devices shown in FIGS. 4 and 6 are concerned, it should be essentially noted that they differ from the embodiment shown in FIG. 3 in that the inlet and outlet of the small control balloon 10 are formed on the same side thereof. Furthermore, and this relatively to FIG. 4, this latter differs (still with respect to FIG. 3) in that the valve means 16 of FIG. 3, responsive to the pressure exerted on the small control balloon 10 is replaced by a variant 16* which forms the subject of the above-mentioned Certificate of Addition Application of pages 8 and 9 of this description (it is a question of application FR-86 05 928) and the detail of which has been shown on a larger scale in FIG. 5.

Of course, a valve means of the type shown in this FIG. 5 may be used not only in the embodiment illustrated in FIG. 4 (which is a variant of figure 6) but also in the embodiment illustrated in FIG. 1 by replacing valve 16 by the above valve 16*.

In each embodiment there exists a non return (or anti reflux) valve 21, of the type called "duck beak" (it is essentially a question of a unidirectional valve comprising resilient normally collapsed lips and made as a single piece with tube 9), formed immediately at the inlet or, in any case, immediately upstream of the small control balloon 10.

Furthermore, in so far as the geometric ratios are concerned between the different elements of the device in the implanted state, such as shown in FIG. 4 and 6, and the skin of the patient, they are substantially identical to those defined in FIG. 1.

Hereafter is described the operation of the device of the invention.

In a first stage, the device is filled with serum and is then implanted in a subcutaneous position. Said device thus implanted can be used only after 8 to b 10 days, which is the time required for the healing process to take place.

Using a syringe, on which is mounted the HUBERT needle 3 and which has a volume greater than the volume of reservoir 6 (including the volume of the injection site 5 and of the connection tube 7), the serum is extracted by pricking the skin of the patient in correspondance with site 5 and this serum is replaced by the analgesic action drug, which is diluted to a concentration defined by the doctor, as a function of the real action it is desired to obtain.

The volume of diluted drug, which may be stored in the reservoir, varies from 20 to 500 cc and even more, depending on the therapeutic needs and is fixed by construction.

By pressing on the small balloon 10 by cutaneous pressure in correspondance with position 14, the analgesic product is injected, under the action of this pressure, into the catheter 13 by passing around the valve rod 16 by expansion of the sheath which grips it.

Release of the finger or manual pressure creates a negative pressure, or depression, in the small balloon 10 (this depression is due to the emptying of the small balloon of the whole of its contents, which emptying is caused by the fact that the analgesic product injected into the catheter does not return to the small balloon controlling the injection, since sheath 17 grips again sealingly about rod 16.

Now, this depression causes suction of the drug stored in the reservoir 6, whose flow into the small balloon 10 is controlled by means of the capillary tube 11 provided with the micro-channel 12.

Thus, drug overdoses are prevented for the volume of drug injected by finger pressure cannot exceed the volume of drug which passes in a given time from reservoir 6 to the small balloon 10 under the action of the pressure difference existing therebetween. This time being defined precisely by the micro-channel 12.

As was described above, the filling time may be 2, 4 or 6 hours and even more, as a function of the desired frequency and injection dose.

With the injectable analgesic volume determined once and for all, the analgesic effect is therefore essentially a function of the dilution (or concentration) of drug in the reservoir.

It goes without saying that, if the analgesic effect were to reveal itself insufficient or if it were simply desired to suppress it, it would be sufficient to suck out the product contained in the reservoir at the level of site 5 and to replace it by a more active (or more concentrated) drug or by serum, respectively.

In so far as the amount of drug is concerned which returns to the storage reservoir through the micro-channel, at the time of pressing the small balloon controlling the injection, it may be considered as being negligible because of the presence of the micro-channel and the shortness of the pressing time.

With the device of the invention, filling of the storage reservoir only takes place on request and at extended intervals, which reduces correspondingly the risks of infection due to daily injections. Thus, the injection catheter may be introduced in an intraspinal position and no longer in a peridural position, which makes it possible to reduce - as already mentioned above - the efficient drug doses by a factor at least equal to 3.

As is clear from the foregoing, the invention is in no wise limited to those of its embodiments and modes of application which have just been described more explicitly; it embraces, on the contrary, all the variants thereof which may occur to a technician skilled in the matter without departing from the scope or spirit of the present invention: in particular, it goes without saying that, although the description has been limited to the repeated and controlled self injection of unitary analgesic doses, the device of the invention applied also to the repeated and controlled self injection of any medicament exerting a therapeutic action other than an analgesic action. In particular, the medicament may be formed by papaverine or regitine which are capable of causing erection of the penis by injection into the spongy substance thereof.

We claim:

1. Device for repeated injection of medicament (20) in unitary doses and at a frequency which is a function of therapeutic treatment needs, said device being implantable in a body of a patient and comprising:
   a site (5) for injection of the medicament (20) implantable below the skin (1) of the patient;
   an external supplying means for supplying said site (5);
   a catheter (13), implantable in a therapeutic action zone of the patient, for injecting each unitary dose of medicament;
   a reservoir (6), made from a flexible plastic material, for storing the medicament, between two restocking operations, by means of said external supplying means and through said site (5);
   a first connection tube (7), made from a flexible plastic material, for connecting said reservoir (6) to said site (5);
   a pre-dosed balloon (10) made from a flexible plastic material;
   a second tube (9) for connecting between said balloon (10) and said reservoir (6), said second tube (9) also being made from a flexible plastic material;
   a capillary, for controlling the flowrate of a medicament disposed upstream of said balloon (10), positioned between said balloon (10) and said reservoir (6), so as to control the filling time of said balloon (10);
   valve means (16), disposed between said balloon (10) and said catheter (13), responsive only to pressure exerted on said balloon (10), said balloon (10) having a volume which is a function of the unitary dose of medicament to be injected through said catheter (13) by pressure exerted upon said balloon (10) by cutaneous digital deformation and forming means for controlling the injection of medicament in cooperation with said valve means (16);
   said valve means (16) comprising a valve rod, a clamping means for holding said valve rod and means for initiating slackening of said clamping means of said valve rod as a result of fluid pressure of medicament exerted by a cutaneous digital control of said balloon (10).

2. Device according to claim 1, wherein said valve means (16) is disposed inside a third tube (17) connecting said balloon to said catheter, said third tube being made from a material which shrinks upon polymerization so that said valve means is clamped sealingly inside said third tube.

3. Device according to claim 2 wherein said first and second tubes are made as a single piece (20*) with three branches, whereby an implantation zone of said reservoir (6) in the body of the patient may be chosen as a function of therapeutic needs, said capillary for controlling the flowrate being disposed in a branch of said piece (20*) which is connected to the balloon (10).

4. Device according to claim 2 wherein said capillary (12) has a diameter and a length defined as a function of the desired flowrate and an external wall sealingly fixed to the internal wall of said second connection tube (9).

5. Device according to claim 2 wherein an inlet and an outlet of said balloon are situated on a same side of said balloon.

6. Device according to claim 1, wherein said valve means (16*) is disposed in the catheter (13) at a distal end thereof, said catheter being made from a material which shrinks upon polymeriation so that said valve means is clamped sealingly by said distal end of the catheter.

7. Device according to claim 6 wherein said first and second tubes are made as a single piece (20*) with three branches, whereby an implantation zone of said reservoir (6) in the body of the patient may be chosen as a function of therapeutic needs, said capillary for controlling the flowrate being disposed in a branch of said piece (20*) which is connected to the balloon (10).

8. Device according to claim 6 wherein said capillary (12) has a diameter and a length defined as a function of the desired flowrate and an external wall sealingly fixed to the internal wall of said second connection tube (9).

9. Device according to claim 6 wherein an inlet and an outlet of said balloon are situated on a same side of said balloon.

10. Device according to claim 1 wherein said capillary (12) has a diameter and a length defined as a function of the desired flowrate and an external wall sealingly fixed to the internal wall of said second connection tube (9).

11. Device according to claim 1 wherein said first and second tubes are made as a single piece (20*) with three branches, whereby an implantation zone of said reservoir (6) in the body of the patient may be chosen as a function of therapeutic needs, said capillary for controlling the flowrate being disposed in a branch of said piece (20*) which is connected to the balloon (10).

12. Device according to claim 11, wherein said three branches form a Y.

13. Device according to claim 1, wherein said three branches form a T.

14. Device according to claim 1, wherein an inlet and an outlet of said balloon are situated on a same side of said balloon.

* * * * *